United States Patent
Reschetilowski et al.

(10) Patent No.: US 10,987,664 B2
(45) Date of Patent: Apr. 27, 2021

(54) PROCESS FOR PREPARING A STRUCTURALLY SELECTIVE OLIGOMERIZATION CATALYST OF PROLONGED STABILITY BY PRECIPITATION

(71) Applicant: Evonik Operations GmbH, Essen (DE)

(72) Inventors: Wladimir Reschetilowski, Radebeul (DE); Felix Alscher, Dresden (DE); Henrik Frenzel, Dresden (DE); Ekaterina Borovinskaya, Pirna (DE); Cornelia Breitkopf, Dresden (DE); Fabian Nadolny, Arnsberg (DE); Guido Stochniol, Haltern am See (DE); Stephan Peitz, Oer-Erkenschwick (DE); Robert Franke, Marl (DE)

(73) Assignee: Evonik Operations GmbH, Essen (DE)

(*) Notice: Subject to any disclaimer, the term of this patent is extended or adjusted under 35 U.S.C. 154(b) by 162 days.

(21) Appl. No.: 16/298,561

(22) Filed: Mar. 11, 2019

(65) Prior Publication Data
US 2019/0283014 A1 Sep. 19, 2019

(30) Foreign Application Priority Data

Mar. 14, 2018 (EP) .................... 18161755

(51) Int. Cl.
| | | |
|---|---|---|
| B01J 37/03 | (2006.01) | |
| B01J 37/04 | (2006.01) | |
| B01J 37/08 | (2006.01) | |
| C01B 39/04 | (2006.01) | |
| B01J 35/10 | (2006.01) | |
| B01J 37/02 | (2006.01) | |
| B01J 37/00 | (2006.01) | |
| B01J 21/12 | (2006.01) | |
| B01J 29/04 | (2006.01) | |
| B01J 29/072 | (2006.01) | |
| C07C 2/12 | (2006.01) | |
| C07C 2/10 | (2006.01) | |
| B01J 35/00 | (2006.01) | |
| C07C 11/08 | (2006.01) | |
| B01J 31/02 | (2006.01) | |
| B01J 23/755 | (2006.01) | |
| B01J 29/46 | (2006.01) | |

(52) U.S. Cl.
CPC .......... *B01J 37/031* (2013.01); *B01J 29/044* (2013.01); *B01J 29/072* (2013.01); *B01J 35/002* (2013.01); *B01J 35/109* (2013.01); *B01J 35/1019* (2013.01); *B01J 35/1023* (2013.01); *B01J 37/0018* (2013.01); *B01J 37/0201* (2013.01); *B01J 37/033* (2013.01); *B01J 37/036* (2013.01); *B01J 37/04* (2013.01); *B01J 37/08* (2013.01); *B01J 37/082* (2013.01); *C01B 39/04* (2013.01); *C07C 2/10* (2013.01); *C07C 2/12* (2013.01); *B01J 21/12* (2013.01); *B01J 23/755* (2013.01); *B01J 29/46* (2013.01); *B01J 31/0238* (2013.01); *B01J 31/0239* (2013.01); *C07C 11/08* (2013.01); *C07C 2529/072* (2013.01)

(58) Field of Classification Search
CPC ...... B01J 37/031; B01J 35/109; B01J 37/033; B01J 35/1019; B01J 35/002; B01J 37/036; B01J 37/0201; B01J 37/082; B01J 37/0018; B01J 35/1023; B01J 29/044; B01J 29/072; B01J 37/04; B01J 37/08; B01J 31/0239; B01J 31/0238; B01J 23/755; B01J 21/12; B01J 29/46; C07C 2/10; C07C 2/12; C07C 11/08; C07C 2529/072; C07C 2/24; C01B 39/04; C10G 50/00

See application file for complete search history.

(56) References Cited

U.S. PATENT DOCUMENTS

| | | | |
|---|---|---|---|
| 5,134,242 A | 7/1992 | Le et al. | |
| 5,260,501 A | 11/1993 | Bhore et al. | |
| 5,849,972 A | 12/1998 | Vicari et al. | |
| 6,346,224 B1 * | 2/2002 | Vitale-Rojas | ......... C01B 39/065 423/328.2 |
| 2016/0243533 A1 * | 8/2016 | Rivas-Cardona | ........ B01J 29/76 |

FOREIGN PATENT DOCUMENTS

WO 1995/14647 6/1995

OTHER PUBLICATIONS

Vitale et al., "One-pot preparation and characterization of bifunctional Ni-containing ZSM-5 catalysts," Applied Catalysis A: General vol. 452, Feb. 15, 2013, 75-87. (Year: 2013).*
U.S. Appl. No. 16/293,717, filed Mar. 6, 2019, Nadolny et al.
U.S. Appl. No. 16/291,144, filed Mar. 4, 2019, Nadolny et al.
U.S. Appl. No. 16/293,859, filed Mar. 6, 2019, Nadolny et al.
U.S. Appl. No. 16/293,702, filed Mar. 6, 2019, Nadolny et al.
Search Report dated Sep. 6, 2019 in European Application No. 19162180.4.
Moussa et al., "*Heterogeneous oligomerization of ethylene to liquids on bifunctional Ni-based catalysts: The influence of support properties on nickel speciation and catalytic performance*," Catalysis Today 277 (2016) 78-88.

* cited by examiner

*Primary Examiner* — Anthony J Zimmer
(74) *Attorney, Agent, or Firm* — Grüneberg and Myers PLLC

(57) ABSTRACT

A process for preparing an oligomerization catalyst is based on using nickel aluminosilicate that has high activity and selectivity coupled with adequate service life in the heterogeneously catalysed oligomerization of C3 to C6 olefins or olefin-containing feed mixtures based thereon.

12 Claims, No Drawings

PROCESS FOR PREPARING A STRUCTURALLY SELECTIVE OLIGOMERIZATION CATALYST OF PROLONGED STABILITY BY PRECIPITATION

CROSS-REFERENCE TO RELATED APPLICATIONS

This application claims priority to European patent application 18161755.6 filed Mar. 14, 2018, incorporated herein by reference.

BACKGROUND OF THE INVENTION

Field of the Invention

The present invention relates to a process for preparing a nickel aluminosilicate that can advantageously be used as oligomerization catalyst for oligomerization of C3 to C6 olefins and mixtures thereof. The present invention further provides for the use of the oligomerization catalyst in a process for oligomerization of C3 to C6 olefins.

Description of the Background Art

In general, oligomerization is understood to mean the reaction of unsaturated hydrocarbons with one another to form correspondingly longer-chain hydrocarbons, called the oligomers. For example, the oligomerization of two olefins each having three carbon atoms can form an olefin having six carbon atoms (hexene). The oligomerization of two molecules with one another is also called dimerization, the oligomerization of three molecules with one another trimerization, etc.

The resulting oligomers are intermediates that are used, for example, for the preparation of aldehydes, carboxylic acids and alcohols. The oligomerization of olefins is conducted on the industrial scale either in homogeneous phase with a dissolved catalyst or heterogeneously over a solid catalyst or with catalysts in a biphasic reaction system.

In the case of the heterogeneously catalysed processes, oligomerization over acidic oligomerization catalysts has long been known. Examples used in industry include acidic zeolites or phosphoric acid on a support. What are obtained here are isomer mixtures of predominantly branched oligomers. For non-acidic, heterogeneously catalysed oligomerization of olefins, which forms mainly linear or lightly branched dimers, nickel compounds on support materials are most frequently used in industry. For instance, WO 95/14647 A1 describes, as catalyst for olefin oligomerization, a nickel catalyst with a support material consisting of the components titanium oxide and/or zirconium oxide, silicon dioxide and optionally aluminium oxide. In the presence of this catalyst, mixtures of linear butenes are oligomerized to $C_8$ olefins with a selectivity of below 75%.

Various processes are known from the prior art for the preparation of oligomerization catalysts. WO 95/14647 A1 discloses, for example, a process for preparing an oligomerization catalyst in which the individual components are precipitated from a solution. However, the catalyst materials prepared therefrom only show acceptable conversions with regard to the formation of n-octenes at elevated temperatures and elevated pressures.

The problem addressed by the present invention was that of providing a novel process by which an oligomerization catalyst having improved properties can be prepared in a simple manner, and which can achieve good conversions and selectivities under moderate conditions when used in the oligomerization of C3 to C6 olefins, with no adverse effect on the service life of the catalyst and mechanical properties such as strength.

SUMMARY OF THE INVENTION

It has been found that, surprisingly, the underlying problem can be solved by a process in which the oligomerization catalyst based on a nickel aluminosilicate is precipitated from a solution containing at least two templates. A catalyst thus prepared, when used in oligomerization, especially the oligomerization of short-chain olefins, leads to high conversions and a high selectivities to give linear oligomerization products.

The process according to the invention for preparing a catalyst based on nickel aluminosilicate having a silicon/aluminium ratio of 8 to 100, preferably 20 to 90, more preferably 30 to 80 and a nickel content of 0.5% to 15% by weight comprises the following steps:
a. preparing a precipitate suspension by dissolving at least two templates A and B, at least one aluminium source, at least one nickel source and at least one silicon source in a water-based solvent, where the individual components are to be selected such that the prepared suspension has a pH of more than 7.5, preferably of more than 8.5 and more preferably of more than 9.5;
b. adjusting the pH of the precipitate suspension by addition of an inorganic acid to a pH in the range from 7.5 to 12;
c. precipitating the catalyst composition out of the precipitate suspension from step b in a pressure-tight vessel, preferably under an autogenous pressure of up to 15 bar absolute, at a temperature of 100 to 180° C.;
d. removing the catalyst composition precipitated in step c;
e. drying and calcining the precipitated catalyst composition;
f. admixing the calcined catalyst composition with a solution containing ammonium ions;
g. drying and calcining the catalyst composition that has been admixed with the solution in step f for preparation of the final catalyst.

DETAILED DESCRIPTION OF THE INVENTION

In step a, relating to the preparation of the precipitate suspension, the at least one aluminium source, the at least one nickel source and the at least one silicon source and the at least two templates A and B are dissolved in a water-based solvent, preferably water. "Dissolving" or "dissolved" in the context of the present invention means not just complete dissolution of a substance in the solvent, but also includes the suspending of a substance in the solvent. All components are either dissolved together or first dissolved separately in the solvent and then combined. If all components, especially the at least one aluminium source, the at least one nickel source and the at least one silicon source, are dissolved together, these can be mixed prior to the addition of the solvent, preferably crushed together with a mortar. During the dissolving of the components in the solvent, the solvent can be stirred with a suitable apparatus, for example a magnetic stirrer. Once the components have been dissolved in the solvent, the precipitate suspension can be stirred further for a certain period, preferably at least 5 minutes. It should be noted here that the individual components are to be selected such that the prepared suspension has a pH of more than 7.5, preferably of more than 8.5 and more preferably of more than 9.5. Preference is therefore given to using basic components.

The composition of the resulting oligomerization catalyst is adjusted via the quantitative ratios in the precipitate suspension. The resulting precipitate suspension obtained in step a preferably contains a total amount of aluminium source, nickel source and silicon source of 5% to 30% by weight, preferably 6% to 20% by weight and more preferably 8% to 15% by weight. The total amount of the templates A and B in the precipitate suspension may be between 5% and 30% by weight, preferably 12% to 25% by weight. The water-based solvent, preferably water, may be present in the precipitate suspension in an amount of 30% to 80% by weight. The molar ratio of silicon to aluminium in the precipitate suspension, which can be controlled via the amount of the silicon source and aluminium source added, can be used to adjust the silicon/aluminium ratio in the finished oligomerization catalyst. The nickel content in the oligomerization catalyst can be adjusted via the amount of nickel to be added to the precipitate suspension with the assumption that the total amount of the aluminium source added is present in the finished oligomerization catalyst as $Al_2O_3$ and the total amount of the silicon source added in the finished oligomerization catalyst as $SiO_2$.

Aluminium sources used in step a may in principle be all aluminium compounds that are soluble, or even only slightly soluble, in the water-based solvent. In a preferred embodiment of the present invention, aluminium sources used may be sodium aluminate, aluminium sulfate, aluminium nitrate or mixtures thereof.

Nickel sources used in step a may in principle be all nickel compounds that are soluble, or even only slightly soluble, in the water-based solvent. In a preferred embodiment of the present invention, the nickel source may be selected from the group consisting of nickel nitrate in anhydrous or hydrated form, nickel halides, for example nickel chloride, and nickel sulfate.

Silicon sources used in step a may in principle be all silicon compounds that are soluble, or even only slightly soluble, in the water-based solvent. In a preferred embodiment of the present invention, the silicon source may be selected from the group consisting of colloidal silicon dioxide, orthosilicates with alkali metal cations, for example sodium orthosilicate or sodium trisilicate, and tetraalkyl orthosilicates, for example tetramethyl orthosilicate or tetraethyl orthosilicate. The silicon source used is preferably sodium orthosilicate or sodium trisilicate.

The templates A and B are structure-directing compounds that are intended to have an assisting effect in the formation of micro- and mesoporous structures. The use of two different templates is intended to trigger the formation of a biporous structure or a bimodal pore size distribution.

Template A here assists the formation of a microporous phase of maximum crystallinity. Template A may be selected from the group consisting of primary amines having 2 to 4 carbon atoms, diamines having 2 to 4 carbon atoms, quaternary ammonium compounds with alkyl groups having 2 to 4 carbon atoms in hydroxidic or halide form, for example tetrapropylammonium hydroxide or tetrapropylammonium bromide. In addition, template A used may also be morpholine or ammonium compounds in combination with ethanol, for example ethanolammonium nitrate. The latter may also be formed in situ by dissolution of an appropriate ammonium compound in an ethanol-containing aqueous solution. Preference is given in accordance with the invention to using quaternary ammonium compounds in aqueous solution as template A, particular preference being given to using tetrapropylammonium hydroxide and tetrapropylammonium bromide dissolved in deionized water as template A.

Template B assists the formation of the x-ray-amorphous mesoporous phase having elevated pore diameter compared to the crystalline microporous phase. Templates B used may be ammonium compounds having four alkyl groups, where at least one of the alkyl groups has an elevated chain length having 10 to 20 carbon atoms. The remaining alkyl groups of the ammonium compounds may be ethyl or methyl groups, preference being given to methyl groups. Suitable anions to the positively charged tetraalkylammonium cation are especially halide or hydroxide ions. Template B used in accordance with the invention is preferably cetyltrimethylammonium bromide or cetyltrimethylammonium hydroxide.

By variation in the molar ratio of template A to template B, it is possible to influence the proportions of the macroporous and mesoporous phases. For this reason, preference is given to a molar ratio of template A to template B in the range from 90:10 to 60:40. In a further-preferred embodiment of the present invention, a molar ratio of template A to template B of 88:12 to 80:20 is used in the preparation of the oligomerization catalyst.

In the subsequent step b, relating to the adjustment of the pH of the precipitate suspension, an inorganic acid is added to the precipitate suspension, preferably while stirring, in order to adjust the pH to a value in the range from 7.5 to 12, preferably from 8.5 to 11.5, more preferably from 9.5 to 11. The inorganic acid is preferably added stepwise, preferably by dropwise addition. In a preferred embodiment of the present invention, the inorganic acid is selected from the group consisting of sulfuric acid, hydrochloric acid, nitric acid or a mixture thereof. The measurement of the pH can be conducted by means of a commercial pH probe with constant stirring.

After the pH has been adjusted in step b, the precipitate suspension is transferred to a pressure-tight vessel and the catalyst composition is precipitated, preferably under an autogenous pressure of up to 15 bar absolute, in step c. The vessel may, for example, be an autoclave. The inner wall of the pressure-tight vessel may have been provided with an inert coating in order to avoid unwanted reactions. For this purpose, it is possible with preference to use Teflon inserts or coatings. The pressure-tight vessel is closed and heated to a temperature of 100 to 180° C., preferably of 130 to 170° C., more preferably of 140 to 160° C. Optionally, the precipitate suspension may be stirred during this time at a low stirring speed, but the stirring should not exceed 200 revolutions per minute. The heating of the precipitate suspension to the desired temperature can establish an autogenous pressure in the pressure-tight vessel of up to 15 bar absolute, which should be maintained. The pressure is preferably 1 to 15 bar absolute. The temperature is preferably maintained for 10 to 180 hours, more preferably for 12 to 72 hours, more preferably for 24 to 55 hours. Subsequently, the pressure-tight vessel is cooled and opened.

The catalyst composition obtained by the precipitation in step c is separated from the remaining solvent in step d by a suitable method. Suitable examples for this purpose are filtration and/or filtration with suction. The precipitated catalyst composition can subsequently be washed, preferably repeatedly, with an excess of water, ethanol or a mixture thereof.

In step e, the precipitated and optionally washed catalyst composition is subsequently dried at a temperature between 30 and 200° C., preferably between 40 and 180° C., more preferably between 50 and 160° C. The duration of the drying is adapted to the drying temperature, and the residual moisture content of the catalyst must not exceed 20%. The residual moisture content describes the percentage loss of mass from a sample when it is heated to 110° C. and kept at that temperature until no change in mass is measurable any longer. This measurement can be conducted with the Moisture Analyzer from Mettler-Toledo. After the drying, the precipitated catalyst composition is calcined in a suitable oven, for reasons including oxidative removal of the templates. The calcination is preferably conducted at a temperature between 400 and 650° C., preferably between 450 and 600° C., more preferably between 475 and 575° C. The calcination can be conducted using an oxygen-containing gas, for example air. The duration of the calcination is dependent on many factors, for example on the amount of template or the amount of gas optionally supplied. Depending on the factors mentioned, the calcination should be conducted until the template has been virtually completely (oxidatively) removed.

After the calcination, the catalyst composition that has been dried and calcined in step e is in the sodium form. In step f, the calcined catalyst composition is admixed with a solution containing ammonium ions in order to convert the catalyst composition to the ammonium form, especially by ammonium ion exchange. The solution containing ammonium ions is preferably an aqueous solution of ammonium nitrate, ammonium hydroxide or ammonium sulfate, more preferably an aqueous solution of ammonium nitrate. The concentration of the ammonium compound in the aqueous solution may be in the range from 0.01 mol/l to 1 mol/l, preferably in the range from 0.05 mol/l to 0.5 mol/l. Step f can be conducted at elevated temperature, especially at a temperature between 30 and 90° C., preferably between 50 and 80° C.

"Ammonium form" in the context of the present invention is understood to mean the state in which, in a formal sense, a negative charge can be assumed to exist on the aluminium atom onto which the ammonium cation can add (see right-hand side of the image below). In the sodium form, the formally negative charge on the aluminium ion is masked by a sodium cation (see left-hand side of the image below).

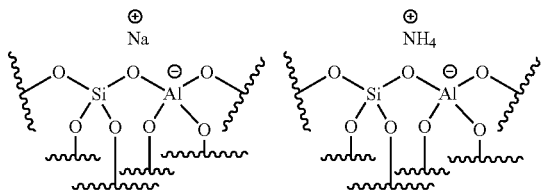

In a preferred embodiment of the present invention, the catalyst composition is converted to the ammonium form in step f with at least 5 times the amount, preferably at least 7 times the amount, more preferably at least 9 times the amount, of aqueous solution containing ammonium ions. The molar ammonium ion excess based on the sodium ions is at least 2 times and not more than 5 times, but preferably 3 times. The catalyst composition need not just be treated once with a solution containing ammonium ions. The solution can also be exchanged once or more than once, especially twice. For this purpose, the catalyst composition is separated from one solution containing unexchanged ammonium ions and contacted with a fresh solution containing the original amount of ammonium ions.

The catalyst composition obtained by step f can subsequently be separated by a suitable method from the remaining solution containing ammonium ions. Suitable examples for this purpose are filtration and/or filtration with suction. The catalyst composition thus removed can subsequently be washed, preferably repeatedly, with an excess of water, ethanol or a mixture thereof.

After step f, the catalyst composition is dried again and calcined in step g in order to obtain the final catalyst composition. The catalyst composition can be dried in step g at a temperature between 30 and 200° C., preferably between 40 and 180° C., more preferably between 50 and 160° C. The duration of the drying is adapted to the drying temperature, and the residual moisture content of the catalyst must not exceed 20%. After the drying, the catalyst composition is calcined in a suitable oven. The calcination is preferably conducted at a temperature between 400 and 650° C., preferably between 450 and 600° C., more preferably between 475 and 575° C. The calcination can be conducted using air, nitrogen, an inert gas, such as argon, or mixtures thereof.

Subsequently, shaping of the calcined catalyst composition may be required to be able to use the oligomerization catalyst industrially as well. The shaping methods include the methods known to those skilled in the art, such as extruding, pelletizing, tableting or compacting. Shaping media used, which can be added to the catalyst composition, may be, for example, various clay minerals, silicas, sheet silicates, aluminas.

An oligomerization catalyst prepared by this process comprises or consists of the nickel aluminosilicate which has been prepared from the aluminium source, the nickel source and the silicon source and has a bimodal pore size distribution and a silicon/aluminium ratio of 8 to 100, preferably 20 to 90, more preferably 30 to 80. The nickel content established via the nickel source, with respect to elemental nickel, is 0.5% to 15% by weight, preferably 1% to 10% by weight, more preferably 2% to 8% by weight, based on the overall composition of the oligomerization catalyst.

The carbon content after the preparation of the oligomerization catalyst according to the invention, which especially also comprises template residues that have not been removed by the calcination, referred to as the TOC (total organic carbon) value and determined with a carbon-sulfur analyser, is 150 to 1000 ppm by weight, preferably 200 to 900 ppm by weight and more preferably 250 to 800 ppm by weight.

The bimodal pore size distribution of the oligomerization catalyst is especially characterized by a crystalline microporous phase and an x-ray-amorphous mesoporous phase, where the micro- and mesoporous phases have different average pore diameters. The crystalline microporous phase of the oligomerization catalyst preferably has an average pore diameter in the range from 0.1 to 2 nm, more preferably in the range from 0.3 to 1 nm, determined by nitrogen physisorption (monolayer). The x-ray-amorphous mesoporous phase of the oligomerization catalyst preferably has an average pore diameter in the range from 2.5 to 10 nm, more preferably in the range from 3 to 5 nm, determined by mercury porosimetry.

Further preferably, the oligomerization catalyst according to the invention has a DOC (degree of crystallinity) of 3% to 50%, preferably 10% to 47.5%, more preferably 20% to 45%, determined from x-ray crystallography measurements. The DOC indicates the proportion of the crystalline phase. The DOC can be determined as follows: first of all, an x-ray powder diffractogram of a sample of the oligomerization catalyst and a reference diffractogram of a sample consisting entirely of the crystalline microporous phase are created. For the plot, the (011) reflections (7.9° 2 theta) in the diffractogram of the sample consisting entirely of the crystalline microporous phase are normalized to 100%. To calculate the DOC, the area ($A_{cryst}$) of the peaks that can be identified as peaks of the crystalline phase on the basis of the reference peaks is divided by the area ($A_{total}$) below the entire signal line including all peaks in the diffractogram and multiplied by 100% as per the following formula:

$$DOC = \frac{A_{cryst}}{A_{total}} \cdot 100\%$$

In a preferred embodiment of the present invention, the oligomerization catalyst has a ratio of the pore volume of the crystalline microporous phase to the pore volume of the x-ray-amorphous mesoporous phase from 0.6 to 1.8, preferably from 0.8 to 1.6, determined by nitrogen physisorption.

The oligomerization catalyst prepared in accordance with the invention preferably has a specific surface area (calculated according to BET) of 300 to 700 m$^2$/g, preferably 350 to 600 m$^2$/g, more preferably of 400 to 550 m$^2$/g. The specific surface area is ascertained by nitrogen physisorption according to DIN ISO 9277 (last update: 2014-01).

The catalyst prepared by the process according to the invention can be used especially for the oligomerization of C3 to C6 olefins, preferably C3 to C5 olefins, more preferably of C4 olefins or olefin-containing feed mixtures based thereon. The olefins or olefin-containing feed mixtures are employed as a reactant stream.

The present invention also provides a process for oligomerization of C3 to C6 olefins, wherein an olefin-containing feed mixture comprising the C3 to C6 olefins is guided over a catalyst in at least one reaction zone, where the catalyst used is a catalyst prepared according to claims 1 to 6 for catalysis of the oligomerization reaction. According to the invention, a reaction zone comprises at least one reactor and at least one distillation column in which the oligomer is formed can be removed. The process according to the invention can also be conducted with two or more reaction zones. The oligomerization preferably takes place in the liquid phase.

Olefins usable for the process according to the invention include C3 to C6 olefins, preferably C3 to C5 olefins, more preferably C4 olefins, or olefin-containing feed mixtures based thereon which may also contain proportions of analogous alkanes. Suitable olefins are inter alia α-olefins, n-olefins and cycloalkenes. The olefins used as reactants are preferably n-olefins. In a particularly preferred embodiment of the present invention, the olefin is n-butene. According to the invention the term "olefin-containing feed mixtures based thereon" is to be understood as encompassing any type of mixtures containing the relevant olefins to be oligomerized in an amount which makes it possible to perform the oligomerization. Olefin-containing feed mixtures preferably contain virtually no further unsaturated compounds and polyunsaturated compounds such as dienes or acetylene derivatives. It is preferable to employ olefin mixtures containing less than 5% by weight, in particular less than 2% by weight, of branched olefins based on the olefin proportion.

It is further preferably to employ olefin-containing feed mixtures containing less than 2% by weight of branched olefins, especially iso-olefins.

Propylene (P3) is produced on a large industrial scale by cracking of naphtha and is a commodity chemical which is readily available. C$_5$ olefins are present in light petroleum fractions from refineries or crackers. Industrial mixtures containing linear C$_4$ olefins include light petroleum fractions from refineries, C$_4$ fractions from FC crackers or steam crackers, mixtures from Fischer-Tropsch syntheses, mixtures from the dehydrogenation of butanes, and mixtures formed by metathesis or from other industrial processes. Mixtures of linear butenes suitable for the process according to the invention are obtainable for example from the C$_4$ fraction of a steamcracker. Butadiene is removed in the first step here. This is accomplished either by extraction or extractive distillation of the butadiene or by selective hydrogenation thereof. In both cases a virtually butadiene-free C$_4$ cut is obtained, raffinate 1. In the second step, isobutene is removed from the C$_4$ stream, for example by preparation of methyl tert-butyl ether (MTBE) by reaction with methanol. Other options include the reaction of the isobutene from the raffinate I with water to afford tert-butanol or the acid-catalysed oligomerization of isobutene to afford diisobutene. The now isobutene-free C$_4$ cut, raffinate II, contains, as desired, the linear butenes and any butanes. The 1-butene may optionally still be removed by distillation. Both fractions, the one comprising but-1-ene or the one comprising but-2-ene, may be used in the process according to the invention.

In a further preferred embodiment, streams of matter containing C$_4$ olefins are supplied to the process as olefin-containing feed mixtures. Suitable olefin-containing feed mixtures include raffinate 1 (butadiene-free C4 cut from the steam cracker) and raffinate II (butadiene-free and isobutene-free C4 cut from the steamcracker).

A further option for producing suitable olefin-containing feed mixtures is that of subjecting raffinate I, raffinate II or a similarly constituted hydrocarbon mixture to hydroisomerization in a reactive column. This may afford inter alia a mixture consisting of 2-butenes, small proportions of 1-butene and possibly n-butane and also isobutane and isobutene.

The oligomerization is generally carried out at a temperature in the range from 50° C. to 200° C., by preference 60° C. to 180° C., preferably in the range from 60° C. to 130° C., and at a pressure of 10 to 70 bar, preferably of 20 to 55 bar. If the oligomerization is to be carried out in the liquid phase the parameters pressure and temperature must to this end be chosen such that the reactant stream (the employed olefins or olefin-containing feed mixtures) is in the liquid phase. The weight-based space velocities (reactant mass per unit catalyst per unit time; weight hourly space velocity (WHSV)) of the olefin-containing feed mixture are in the range between 1 g of reactant per g of catalyst and per h (=1 h$^{-1}$) and 190 h$^{-1}$, preferably between 2 h$^{-1}$ and 35 h$^{-1}$, more preferably between 3 h$^{-1}$ and 25 h$^{-1}$.

In one embodiment of the present invention, the degree of dimerization (also referred to as "percentage selectivity based on dimerization") after the oligomerization based on the converted reactant is at least 60%, more preferably at least 75%, more preferably at least 80%.

The linearity of an oligomerization product/of the dimers formed is described by the iso index and represents a value for the average number of methyl branches in the dimer. For example (for butene as the reactant), n-octenes contribute 0, methylheptenes contribute 1 and dimethylhexenes contribute 2 to the iso index of a C8 fraction. The lower the iso index, the more linear the construction of the molecules in the respective fraction. The iso index is calculated by the following general formula:

$$\frac{\text{(singly branched dimers (\% by wt)} + 2 \times \text{doubly branched dimers (\% by weight))}}{100}$$

Accordingly, a dimer mixture having an iso index of 1.0 has an average of exactly 1 methyl branch per dimeric molecule.

The iso index of the product from the oligomerization process according to the invention is preferably 0.8 to 1.2, more preferably 0.8 to 1.15.

The oligomers produced by the process according to the invention are utilized inter alia for producing aldehydes, alcohols and carboxylic acids. Thus for example the dimerizate of linear butenes affords a nonanal mixture by hydroformylation. This provides either the corresponding carboxylic acids by oxidation or a $C_9$ alcohol mixture by hydrogenation. The $C_9$ acid mixture may be used for producing lubricants or siccatives. The $C_9$ alcohol mixture is a precursor for the production of plasticizers, particularly dinonyl phthalates, or DINCH.

Even without further elaboration it is assumed that a person skilled in the art will be able to utilize the description above to the greatest possible extent. The preferred embodiments of the present invention and examples are therefore to be interpreted merely as a descriptive disclosure which is not to be regarded as limiting in any way.

The present invention is more particularly elucidated hereinbelow with reference to examples. Alternative embodiments of the present invention are obtainable analogously.

EXAMPLES

Catalyst Synthesis (Inventive Catalyst 1):

In the synthesis, cetyltrimethylammonium bromide, tetrapropylammonium bromide, sodium aluminate, nickel nitrate hexahydrate and sodium trisilicate were dissolved in deionized water and stirred until a milky white, pale greenish solution had formed. The sodium trisilicate was added in a 40-fold molar excess based on one silicon atom by comparison with sodium aluminate. The solution was adjusted to a pH of about 10 by adding sulfuric acid dropwise. Subsequently, the solution was introduced into an autoclave with a Teflon insert and heated to 130 to 170° C., which resulted in precipitation of the catalyst composition. After the precipitation, the precipitated catalyst was filtered off and washed with water and ethanol. For removal of the templates, the catalyst composition was first dried and then calcined at >500° C. Thereafter, the catalyst composition was treated at least twice with an ammonium nitrate solution at >50° C. Thereafter, a further drying operation and the final calcination at >400° C. were effected.

The catalyst thus prepared had a nickel content of 3% by weight and an Si/Al ratio of 40.

Catalyst Synthesis (Inventive Catalyst 2):

The synthesis was conducted as for catalyst 1, except that the sodium silicate was added in 10 times the amount. The catalyst thus prepared had a nickel content of 3% by weight and an Si/Al ratio of 10.

Catalyst Synthesis (Inventive Catalyst 3):

The synthesis was conducted as for catalyst 1, except that the sodium silicate was added in 70 times the amount. The catalyst thus prepared had a nickel content of 3% by weight and an Si/Al ratio of 70.

Catalyst Synthesis (Noninventive Catalyst 4):

The synthesis was conducted as for catalyst 1, except that no sodium aluminate was added. The catalyst thus prepared had a nickel content of 3% by weight. No Si/Al ratio can be determined since no Al is present.

Use of the Catalysts in the Oligomerization:

About 12 g of the catalyst in each case were introduced into a metal tube having an internal diameter of 6 mm. Added in front of and behind the catalyst were glass beads having a diameter of 2 mm, which serve as a pre-heating and cooling phase. The oligomerization was conducted using two different feed streams at 30 bar and a loading of 7.5 g/h of butene per gram of catalyst, with variation of the reaction temperature between 80° C. and 100° C. The products were analysed by gas chromatography for the conversion of butenes and the linearity of the octenes. The compositions of the feed stream for the oligomerization are shown in Table 1 below.

The conversions and selectivities achieved for the feed stream as a function of temperature for catalysts 1 to 3 (inventive) and catalyst 4 (noninventive) and the iso indices resulting therefrom are reported in Tables 2 to 5.

TABLE 1

| Composition of feed stream | |
|---|---|
| | Feed stream 1 |
| isobutane | 8.0% |
| n-butane | 15.3% |
| trans-2-butene | 27.9% |
| 1-butene | 32.7% |
| isobutene | 0.9% |
| cis-2-butene | 15.2% |

TABLE 2

Conversion and iso index in oligomerization using catalyst 1
Loading (feed of C4 olefins in g/h per unit mass of catalyst in g) as WHSV: 7.5 h$^{-1}$

| | Temperature | Conversion based on C4 olefins | Iso index |
|---|---|---|---|
| Catalyst 1 (inventive) | 80° C. | 7.8% | 0.92 |

TABLE 3

Conversion and iso index in oligomerization using catalyst 2
Loading (feed of C4 olefins in g/h per unit mass of catalyst in g) as WHSV: 7.5 $^{-1}$

| | Temperature | Conversion based on C4 olefins | Iso index |
|---|---|---|---|
| Catalyst 2 (inventive) | 80° C. | 3.0% | 0.90 |

TABLE 4

Conversion and iso index in oligomerization using catalyst 3
Loading (feed of C4 olefins in g/h per unit mass of catalyst
in g) as WHSV: 7.5 h$^{-1}$

| | Temperature | Conversion based on C4 olefins | Iso index |
|---|---|---|---|
| Catalyst 3 (inventive) | 80° C. | 9.1% | 0.87 |

TABLE 5

Conversion and iso index in oligomerization using catalyst 4
Loading (feed of C4 olefins in g/h per unit mass of catalyst
in g) as WHSV: 7.5 h$^{-1}$

| | Temperature | Conversion based on C4 olefins | Iso index |
|---|---|---|---|
| Catalyst 4 (noninventive) | 80° C. | 2.2% | 0.87 |

By contrast with noninventive catalyst 4, it was surprisingly found that inventive catalysts 1 to 3 can achieve a noticeable rise in conversion with similar iso indices.

The invention claimed is:

1. A process for preparing a nickel aluminosilicate catalyst having a silicon/aluminium ratio of 8 to 100 and a nickel content of 0.5% to 15% by weight, wherein the process comprises:
   a. preparing a precipitate suspension by dissolving at least two templates A and B, at least one aluminium source, at least one nickel source and at least one silicon source in a water-based solvent, wherein the individual components are to be selected such that the prepared suspension has a pH of more than 8.5;
   b. adjusting the pH by addition of an inorganic acid to a pH in the range from 7.5 to 12;
   c. precipitating the catalyst composition out of the precipitate suspension from step b in a pressure-tight vessel at a temperature of 100 to 180° C.;
   d. removing the catalyst composition precipitated in step c, to obtain a precipitated catalyst composition;
   e. drying and calcining the precipitated catalyst composition, to obtain a calcined catalyst composition;
   f. admixing the calcined catalyst composition with a solution containing ammonium ions;
   g. drying and calcining the catalyst composition that has been admixed with the solution in step f, to obtain said nickel aluminosilicate catalyst having a silicon/aluminium ratio of 8 to 100 and a nickel content of 0.5% to 15% by weight.

2. The process according to claim 1, wherein the aluminium source is at least one selected from the group consisting of sodium aluminate, aluminium sulfate, aluminium nitrate and mixtures thereof.

3. The process according to claim 1, wherein the nickel source is at least one selected from the group consisting of nickel nitrate in anhydrous or hydrated form, nickel halides and nickel sulfate.

4. The process according to claim 1, wherein the silicon source is at least one selected from the group consisting of colloidal silicon dioxide, orthosilicates with alkali metal cations, and tetraalkyl orthosilicates.

5. The process according to claim 1, wherein template A is selected from the group consisting of primary amines having 2 to 4 carbon atoms, diamines having 2 to 4 carbon atoms, quaternary ammonium compounds with alkyl groups having 2 to 4 carbon atoms in hydroxidic or halide form, and mixtures thereof.

6. The process according to claim 1, wherein template B used is an ammonium compound having four alkyl groups, wherein at least one of the alkyl groups has an elevated chain length having 10 to 20 carbon atoms.

7. The process according to claim 1, wherein the catalyst has a silicon/aluminium ratio of 20 to 90.

8. The process according to claim 1, wherein the catalyst has a silicon/aluminium ratio of 30 to 80.

9. The process according to claim 1, wherein the precipitate suspension prepared in step a contains a total amount of aluminium source, nickel source and silicon source of 5% to 30% by weight.

10. The process according to claim 1, wherein the total amount of templates A and B in the precipitate suspension prepared in step a is between 5% and 30% by weight.

11. The process according to claim 1, wherein the precipitate suspension prepared in step a contains the water-based solvent in an amount of 30% to 80% by weight.

12. The process according to claim 1, wherein the precipitating of the catalyst suspension out of the precipitate suspension in step c is effected under an autogenous pressure of up to 15 bar.

* * * * *